US011033476B2

(12) United States Patent
Gronlund et al.

(10) Patent No.: US 11,033,476 B2
(45) Date of Patent: *Jun. 15, 2021

(54) ORAL CARE COMPOSITIONS AND METHODS FOR WHITENING TEETH

(71) Applicant: Colgate-Palmolive Company, New York, NY (US)

(72) Inventors: Jennifer Gronlund, Flemington, NJ (US); Guofeng Xu, Plainsboro, NJ (US); Venda Porter Maloney, Piscataway, NJ (US); Junhong Mao, Plainsboro, NJ (US); Shaotang Yuan, East Brunswick, NJ (US); Suman Chopra, Monroe, NJ (US); Jodie Parker, Parsippany, NJ (US); Rajnish Kohli, Hillsborough, NJ (US); Robert Dicosimo, Chadds Ford, PA (US); Kari A. Fosser, Folsom, CA (US); Sharon L. Haynie, Philadelphia, PA (US); Mark S. Payne, Wilmington, DE (US); John T. Gannon, Hockessin, DE (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/566,932

(22) Filed: Sep. 11, 2019

(65) Prior Publication Data

US 2019/0388327 A1 Dec. 26, 2019

Related U.S. Application Data

(63) Continuation of application No. 15/838,776, filed on Dec. 12, 2017, now Pat. No. 10,413,500.

(60) Provisional application No. 62/436,828, filed on Dec. 20, 2016.

(51) Int. Cl.
| | | |
|---|---|---|
| *A61K 8/66* | (2006.01) |
| *A61K 8/81* | (2006.01) |
| *A61K 8/37* | (2006.01) |
| *A61K 8/25* | (2006.01) |
| *A61Q 11/00* | (2006.01) |
| *A61K 8/22* | (2006.01) |

(52) U.S. Cl.
CPC ............ *A61K 8/66* (2013.01); *A61K 8/22* (2013.01); *A61K 8/25* (2013.01); *A61K 8/37* (2013.01); *A61K 8/8176* (2013.01); *A61Q 11/00* (2013.01); *A61K 2800/31* (2013.01); *A61K 2800/48* (2013.01); *A61K 2800/57* (2013.01)

(58) Field of Classification Search
CPC .. A61K 2800/57; A61K 2800/48; A61K 8/22; A61K 8/25; A61K 8/8176; A61K 8/66; A61K 8/37; A61K 2800/31; A61Q 11/00
See application file for complete search history.

(56) References Cited

U.S. PATENT DOCUMENTS

| | | | |
|---|---|---|---|
| 4,931,273 A * | 6/1990 | Gaffar ................. | A61K 8/24 424/52 |
| 5,989,526 A | 11/1999 | Aaslyng et al. | |
| 6,221,341 B1 | 4/2001 | Montgomery | |
| 6,723,304 B2 | 4/2004 | Stier | |
| 7,189,385 B2 | 3/2007 | Montgomery | |
| 7,510,859 B2 | 3/2009 | Wieland et al. | |
| 8,389,254 B2 | 3/2013 | Dicosimo et al. | |
| 8,735,125 B2 * | 5/2014 | Dicosimo ............ | C12N 9/18 435/197 |
| 8,841,098 B2 | 9/2014 | Payne et al. | |
| 8,932,563 B2 * | 1/2015 | Martinetti .......... | A61K 8/365 424/49 |
| 9,884,000 B2 | 2/2018 | Boyd et al. | |
| 10,098,824 B2 | 10/2018 | Boyd et al. | |
| 10,413,500 B2 * | 9/2019 | Gronlund ............ | A61Q 11/00 |
| 10,426,719 B2 * | 10/2019 | Yuan .................. | A61K 8/8176 |
| 2006/0045854 A1 | 3/2006 | Zaidel et al. | |
| 2006/0182695 A1 | 8/2006 | Montgomery | |
| 2007/0071695 A1 | 3/2007 | Chopra et al. | |
| 2011/0236859 A1 | 9/2011 | Keleman et al. | |
| 2012/0317731 A1 | 12/2012 | Jiang et al. | |
| 2012/0328534 A1 | 12/2012 | Butterick et al. | |
| 2014/0193562 A1 * | 7/2014 | Popplewell .......... | A23L 2/56 426/535 |
| 2014/0338688 A1 | 11/2014 | Boyd et al. | |
| 2015/0118167 A1 | 4/2015 | Boyd et al. | |
| 2018/0168972 A1 | 6/2018 | Yuan et al. | |
| 2018/0168973 A1 | 6/2018 | Hassan et al. | |
| 2018/0168983 A1 * | 6/2018 | Pillai .................. | A61K 8/442 |
| 2018/0168993 A1 | 6/2018 | Yuan et al. | |
| 2019/0388326 A1 * | 12/2019 | Yuan .................. | A61Q 11/00 |

FOREIGN PATENT DOCUMENTS

| | | |
|---|---|---|
| TW | 201424767 | 7/2014 |
| WO | 2005/056782 | 6/2005 |
| WO | 2007/054203 | 5/2007 |
| WO | 2012/087970 | 6/2012 |
| WO | 2013/096318 | 6/2013 |
| WO | 2013/096321 | 6/2013 |
| WO | 2013/148190 | 10/2013 |

* cited by examiner

OTHER PUBLICATIONS

Dentifrice—Wikipedia. Two (2) pages downloaded from https://en.wikipedia.org/wiki/Dentifrice on Feb. 13, 2019 (Year:2019).

*Primary Examiner* — Ganapathirama Raghu

(57) ABSTRACT

An oral care composition including an orally acceptable vehicle is disclosed. The orally acceptable vehicle includes a source of hydrogen peroxide, an acyl donor, and an enzyme that catalyzes the generation of peracetic acid between the source of hydrogen peroxide and the acyl donor.

20 Claims, No Drawings

Specification includes a Sequence Listing.

SEQUENCE LISTING

```
<160> NUMBER OF SEQ ID NOS: 3

<210> SEQ ID NO 1
<211> LENGTH: 325
<212> TYPE: PRT
<213> ORGANISM: Thermotoga maritima

<400> SEQUENCE: 1

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
        165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220
```

```
Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
        260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 2
<211> LENGTH: 318
<212> TYPE: PRT
<213> ORGANISM: Bacillus subtilis

<400> SEQUENCE: 2

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Leu His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270
```

```
Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 3
<211> LENGTH: 5
<212> TYPE: PRT
<213> ORGANISM: Artificial Sequence
<220> FEATURE:
<223> OTHER INFORMATION: Motif in CE-7 family
<220> FEATURE:
<221> NAME/KEY: misc_feature
<222> LOCATION: (2)..(2)
<223> OTHER INFORMATION: Xaa is any amino acid residue

<400> SEQUENCE: 3

Gly Xaa Ser Gln Gly
1               5
```

ORAL CARE COMPOSITIONS AND METHODS FOR WHITENING TEETH

CROSS REFERENCE TO RELATED APPLICATIONS

This application claims the benefit of U.S. patent application Ser. No. 15/838,776, filed on Dec. 12, 2017, and issued as U.S. Pat. No. 10,413,500, which claimed the benefit of U.S. provisional Patent Application Ser. No. 62/436,828, filed on Dec. 20, 2016, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on 13 Dec. 2016, is named 10662-00-US-P1-OC_ST25.text and is 7000 bytes in size.

BACKGROUND

Conventional oral care products (e.g., toothpastes, gels, etc.) including oral care whitening agents are often utilized to whiten teeth. For example, conventional toothpastes including hydrogen peroxide are often utilized to oxidize chromophores bound to surfaces of teeth to thereby whiten the teeth. While toothpastes including hydrogen peroxide have proven to be effective for whitening teeth, different chromophores on the surfaces are often oxidized at varying rates and/or via varying mechanisms. Accordingly, toothpastes including a single whitening agent (e.g., hydrogen peroxide) may require relatively longer periods of treatment to appreciably whiten the teeth.

In view of the foregoing, oral care products incorporating hydrogen peroxide often include an additional oral care whitening agent to facilitate the oxidation of the different chromophores to thereby shorten the periods of treatment. While the oral care products incorporating a variety of whitening agents have demonstrated increased efficacy in whitening teeth, there is a desire to utilize whitening agents having relatively increased reactivity to thereby further reduce the periods of treatment. However, the oral care whitening agents having relatively increased reactivity are often unstable and subject to degradation. For example, the oral care whitening agents having relatively increased reactivity often react with other components of the dentifrice and/or degrade, thereby reducing the effectiveness thereof.

What is needed, then, are improved oral care whitening compositions and methods for whitening teeth.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition, including an orally acceptable vehicle, wherein the orally acceptable vehicle includes a source of hydrogen peroxide, an acyl donor, and vehicle and an enzyme that catalyzes the generation of peracetic acid between the source of hydrogen peroxide and the acyl donor.

In one implementation, the enzyme has perhydrolytic activity and is configured to generate peracetic acid via enzyme-catalyzed perhydrolysis.

In another implementation, the source of hydrogen peroxide is a cross-linked polyvinylpyrrolidone (PVP) hydrogen peroxide complex.

In another implementation, the whitening complex is substantially free of water.

In another implementation, the acyl donor is selected from one or more of a $C_{2-18}$ carboxylic acid, a hydrolysable ester, and mixtures thereof.

In another implementation, the acyl donor is triacetin.

In another implementation, the oral care composition includes a thickening system, optionally the thickening system includes a silica thickener, further optionally the thickening system includes fumed silica.

In another implementation, the enzyme comprises a CE-7 signature motif that aligns with SEQ ID NO: 2 using, e.g., CLUSTALW, the CE-7 signature motif comprising a) an RGQ motif at positions corresponding to positions 118-120 of SEQ ID NO: 2; b) a GXSQG (SEQ ID NO: 3) motif at positions corresponding to positions 179-183 of SEQ ID NO: 2 and an HE motif at positions corresponding to positions 298-299 of SEQ ID NO:2.

In another implementation, the enzyme comprises an amino acid sequence comprising a CE-7 signature motif and having at least 80% amino acid sequence identity to SEQ ID NO:1.

In another implementation, the oral care composition is in the form of a gel or a paste.

In another implementation, the orally acceptable vehicle includes a dentifrice and an oral care whitening booster, wherein the dentifrice includes the source of hydrogen peroxide, and the oral care whitening booster includes the acyl donor and the enzyme.

In another implementation, the oral care whitening booster is a gel, and the dentifrice is a paste.

In another implementation, a weight ratio of the dentifrice to the oral care whitening booster is from about 1:1 to about 8:1, optionally about 3:1 to about 6:1, and further optionally about 4:1.

In another implementation, the dentifrice and the oral care whitening booster are configured to be maintained separate from one another until a time of use.

In another implementation, the source of hydrogen peroxide and the acyl donor are each present in an amount effective to generate a maximum amount of about 0.2 wt % peracetic acid based on a total weight of the oral care composition.

In another implementation, the enzyme comprises SEQ ID NO:1.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF BIOLOGICAL SEQUENCES

SEQ ID NO: 1 is the amino acid sequence of *Thermotoga maritima* C277S variant perhydrolase (also referred to herein as EZ-1).

SEQ ID NO: 2 is the amino acid sequence of a cephalosporin C deacetylase from *Bacillus sublilis* ATCC® 31954™.

SEQ ID NO: 3 is a motif, GXSQG, wherein X is any amino acid residue. This motif is shared among members of the carbohydrate esterase family 7 (CE-7 family).

DETAILED DESCRIPTION

The following description of various aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Oral Care Compositions

Compositions disclosed herein may be or include an oral care product or oral care composition and/or an oral care whitening composition thereof. The oral care composition may include one or more sources of hydrogen peroxide, one or more acyl donors, one or more enzymes having perhydolytic activity, and combination and mixtures thereof. The oral care composition may also include a dentifrice containing at least the source of hydrogen peroxide, and an oral care whitening booster containing at least the one or more acyl donors and/or the one or more enzymes having perhydrolytic activity. The dentifrice and the oral care whitening booster of the oral care composition may be maintained separate from one another until the time of use, where they may be combined, mixed, or otherwise contacted with one another. For example, the dentifrice and the oral care whitening booster may be maintained in separate vessels or containers. The dentifrice and the oral care whitening booster may also be combined with one another in a single vessel. As further described herein, the one or more enzymes having perhydolytic activity catalyze a reaction between the one or more sources of hydrogen peroxide and the one or more acyl donors to generate an oral care whitening enhancer (e.g., peracetic acid).

In at least one implementation, any one or more of the sources of hydrogen peroxide, the acyl donors, and/or the enzymes having perhydolytic activity may be maintained separate from one another until the point of use, and at the point of use, the sources of hydrogen peroxide, the acyl donors, and/or the enzymes having perhydolytic activity may be combined, mixed, or otherwise contacted with one another. For example, the sources of hydrogen peroxide may be maintained separate from the acyl donor and/or the enzymes having perhydolytic activity. In another example, the acyl donor may be maintained separate from the sources of hydrogen peroxide and/or the enzyme. In yet another example, the enzymes having perhydolytic activity may be maintained separate from the sources of hydrogen peroxide and/or the acyl donor. Any one or more of the sources of hydrogen peroxide, the acyl donors, and/or the enzymes having perhydolytic activity may be maintained in separate phases or components of the oral care composition until the point of use. For example, any one or more of the sources of hydrogen peroxide, the acyl donors, and/or the enzymes having perhydolytic activity may be maintained in a first phase (e.g., hydrophilic phase) and the remaining one or more of the sources of hydrogen peroxide, the acyl donors, and/or the enzymes having perhydolytic activity may be maintained in a second phase (e.g., hydrophobic phase). In at least one implementation, the sources of hydrogen peroxide may be maintained in a dentifrice (e.g., toothpaste) and the acyl donors and/or the enzymes having perhydolytic activity may be maintained in an oral care whitening booster (e.g., gel, paste, liquid, powder, etc.).

The weight ratio of the dentifrice, including the source of hydrogen peroxide, to the oral care whitening booster, including the acyl donors and/or the enzymes having perhydolytic activity, may be greater than or equal to about 1:1 and less than or equal to about 8:1. For example, the weight ratio of the dentifrice to the whitening booster may be from about 1:1, about 1.5:1, about 2:1, about 2.5:1, about 3:1, about 3.5:1, or about 4:1 to about 4.5:1, about 5:1, about 5.5:1, about 6:1, about 6.5:1, about 7:1, about 7.5:1, or about 8:1. In another example, the weight ratio of the dentifrice to the whitening booster may be from about 1:1 to about 8:1, about 1.5:1 to about 7.5:1, about 2:1 to about 7:1, about 2.5:1 to about 6.5:1, about 3:1 to about 6:1, about 3.5:1 to about 5.5:1, about 4:1 to about 5:1, or about 3.8:1 to about 4.2:1. In yet another example, the weight ratio of the dentifrice to the whitening booster may be greater than 0 and less than 1:1, less than 1.5:1, less than 2:1, less than 2.5:1, less than 3:1, less than 3.5:1, less than 4:1, less than 4.5:1, less than 5:1, less than 5.5:1, less than 6:1, less than 6.5:1, less than 7:1, less than 7.5:1, or less than 8:1. In a typical implementation, the weight ratio of the dentifrice to the whitening booster is about 4:1.

The oral care composition prior to use may be anhydrous. For example, the oral care composition may be free or substantially free of water. As used herein, "free" or "substantially free" may refer to a composition that contains less than 5.0 wt %, less than 3.0 wt %, less than 1.0 wt %, less than 0.1 wt %, less than 0.05 wt %, less than 0.01 wt %, less than 0.005 wt %, or less than 0.0001 wt % based on a total weight of the oral care composition. In at least one implementation, contacting at least a portion of the oral care composition with water may release hydrogen peroxide. For example, contacting the dentifrice (e.g., toothpaste) containing the sources of hydrogen peroxide with water may initiate the release of hydrogen peroxide. In another implementation, the oral care whitening booster including the enzyme may be free or substantially free of water.

Sources of Hydrogen Peroxide

The oral care composition may include one or more sources of hydrogen peroxide. The one or more sources of hydrogen peroxide may be any compound or material configured to react with any one or more of the acyl donors and/or any one or more of the enzymes having perhydolytic activity to form the whitening enhancer. Illustrative sources of hydrogen peroxide may be or include, but are not limited to, hydrogen peroxide, urea peroxide, calcium peroxide, cross-linked polyvinylpyrrolidone (PVP) hydrogen peroxide complex, sodium percarbonate, and the like, and combinations thereof. The sources of hydrogen peroxide may also be or include, but are not limited to, PEROXYDONE™ XL 10 complex, POLYPLASDONE® XL 10F, which are commercially available from Ashland Inc. of Covington, Ky. In a typical implementation, the source of hydrogen peroxide includes cross-linked PVP peroxide.

The amount or concentration of the source of hydrogen peroxide may vary widely. In at least one example, the amount of the source of hydrogen peroxide may be greater than or equal to 0.5 wt % and less than or equal to 10.5 wt % based on a total weight of the oral care whitening composition. For example, the amount of the source of hydrogen peroxide in the whitening composition may be from about 0.5 wt %, about 1.0 wt %, about 1.5 wt %, about 2.0 wt %, about 2.5 wt %, about 2.0 wt %, about 2.5 wt %, about 3.0 wt %, about 3.5 wt %, about 4.0 wt %, about 4.5 wt %, or about 5.0 wt % to about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, about 10.0 wt %, or about 10.5 wt %. In another example, the amount of the source of hydrogen peroxide in the oral care whitening composition may be from about 0.5 wt % to about 10.5 wt %, about 1.0 wt % to about 10.0 wt %, about 1.5 wt % to about 9.5 wt %, about 2.0 wt % to about 9.0 wt %, about 2.5 wt % to about 8.5 wt %, about 2.0 wt % to about 8.0 wt %, about 2.5 wt % to about 7.5 wt %, about 3.0 wt % to about 7.0 wt %, about 3.5 wt % to about 6.5 wt %, about 4.0 wt % to about 6.0 wt %, about 4.5 wt % to about 5.5 wt %, or about 5.0 wt % to about 6.0 wt %. In yet another example, the amount of the source of hydrogen peroxide in the oral care whitening composition may be less than or equal to 0.5 wt %, less than or equal to 1.0 wt %, less than or equal to 1.5 wt %, less than or equal to 2.0 wt %, less than or equal to 2.5 wt %, less than or equal to 2.0 wt %, less than or equal to 2.5 wt %, less than or equal to 3.0 wt %, less than or equal to 3.5 wt %, less than or equal to 4.0 wt %, less than or equal to 4.5 wt %, less than or equal to 5.0 wt %, less than or equal to 5.5 wt %, less than or equal to 6.0 wt %, less than or equal to 6.5 wt %, less than or equal to 7.0 wt %, less than or equal to 7.5 wt %, less than or equal to 8.0 wt %, less than or equal to 8.5 wt %, less than or equal to 9.0 wt %, less than or equal to 9.5 wt %, less than or equal to 10.0 wt %, or less than or equal to 10.5 wt %. In a typical implementation, the amount of the source of hydrogen peroxide in the oral care whitening composition may be about 5.5 wt %.

Acyl Donor

The oral care composition may include one or more acyl donors. The one or more acyl donors may be any compound or material configured to react with any one or more of the sources of hydrogen peroxide and/or any one or more of the enzymes having perhydolytic activity to form the oral care whitening enhancer. The acyl donors may be or include, but are not limited to, $C_{2-18}$ carboxylic acids, including lower linear or branched alkyl carboxylic acids, hydrolysable esters of $C_{2-18}$ carboxylic acids, and the like, and mixtures or combinations thereof. In at least one example, the $C_{2-18}$ carboxylic acids may be unsubstituted. In another example, the $C_{2-18}$ carboxylic acids may be substituted with a hydroxyl and/or a $C_{1-4}$ alkoxy group.

The one or more of the acyl donors may be an ester represented by formula (1),

$$[X]_m R_5 \tag{1}$$

$$R_6 C(O)O \tag{2}$$

where X is an ester group represented by the formula (2), $R_5$ is a $C_{1-6}$ linear, branched, or cyclic hydrocarbyl moiety, a five-member cyclic heteroaromatic moiety, or a six-member cyclic aromatic or heteroaromatic moiety, optionally substituted with hydroxyl groups, where each individually carbon atom in $R_5$ includes no more than one hydroxyl group, no more than one ester group, no more than one ester group or carboxylic acid group, where $R_5$ optionally includes one or more ether linkages, where m is an integer from 1 to the number of carbon atoms in $R_5$, and where the esters have a solubility in water of at least 5 ppm at 25° C.; where $R_6$ is a $C_1$ to $C_7$ linear, branched or cyclic hydrocarbyl moiety, optionally substituted with a hydroxyl group or $C_1$ to $C_4$ alkoxy group, wherein $R_6$ optionally includes one or more ether linkages where $R_6$ is $C_2$ to $C_7$.

In one example, the one or more of the acyl donors may be a glyceride represented by the formula (3),

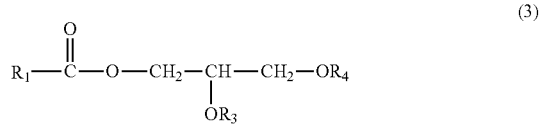

where $R_1$ is a $C_{1-7}$ straight or branch chain alkyl, optionally substituted with a hydroxyl or a $C_{1-4}$ alkoxy group, and $R_3$ and $R_4$ are individually an H or an $R_1C(O)$.

In another example, one or more of the acyl donors may be an ester represented by the formula (4),

where $R_1$ is a $C_{1-7}$ straight or branch chain alkyl, optionally substituted with a hydroxyl or a $C_{1-4}$ alkoxy group, $R_2$ is a $C_{1-10}$ straight or branch chain alkyl, alkenyl, alkynyl, aryl, alkylaryl, alkylheteroaryl, heteroaryl, $(CH_2CH_2O)_n$, or $(CH_2CH(CH_3)—O)_nH$, and n is an integer from 1 to 10.

In yet another example, one or more of the acyl donors may be an acetylated saccharide. Illustrated acetylated saccharides may be or include, but is not limited to, acetylated monosaccharides, acetylated disaccharides, acetylated polysaccharide, and the like, and combinations thereof.

The one or more of the acyl donors may be or include, but is not limited to, $C_{2-18}$ carboxylic acids, $C_{2-6}$ carboxylic acids (e.g., acetic acid), including lower linear or branched alkyl carboxylic acids, optionally substituted with hydroxy and/or $C_{1-4}$ alkoxy groups, hydrolysable and acceptable esters thereof (e.g., mono-, di-, and tri-glycerides, and acylated saccharides), and mixtures thereof. In at least one example, the acyl donors may be or include, but are not limited to 1,2,3-triacetoxypropane or triacetin or glycerin triacetate, acylated saccharides, an the like, and combinations thereof. In at least one implementation, the acyl donor or ester may have a water solubility of at least 5 ppm at 25° C. In a typical implementation, the acyl donor is 1,2,3-triacetoxypropane or triacetin.

In at least one implementation, the acyl donors may be or include, but are not limited to, one or more acylated saccharides selected from acylated mono-, di-, and polysaccharides. In another implementation, the acylated saccharides are selected from acetylated xylan, fragments of acetylated xylan, acetylated xylose (e.g., xylose tetraacetate), acetylated glucose (e.g., α-D-glucose pentaacetate, β-D-glucose pentaacetate, 1-thio-β-D-glucose-2,3,4,6-tetraacetate), β-D- galactose pentaacetate, sorbitol hexaacetate, sucrose octaacetate, β-D-ribofuranose-1,2,3,5-tetraacetate, β-D-ribofuranose-1,2,3,4-tetraacetate, tri-O-acetyl-D-galactal, tri-O-acetyl-D-glucal, 3-D-xylofuranose tetraacetate, β-D-glucopyranose pentaacetate, β-D-glucopyranose-1,2,3,4-tetraacetate, β-D-glucopyranose-2,3,4,6-tetraacetate, 2-acetamido-2-deoxy-1,3,4,6-tetracetyl-β-D-glucopyranose, 2-acetamido-2-deoxy-3,4,6-triacetyl-1-chloride-α-D-glucopyranose, β-D-mannopyranose pentaacetate, and acetylated cellulose. In a typical implementation, the acetylated saccharide is selected from β-D-ribofuranose-1,2,3,5-tetraacetate, tri-O-acetyl-D-galactal, tri-O-acetyl-D-glucal, sucrose octaacetate, and acetylated cellulose. In another implementation, the acyl donors may include 5-acetoxymethyl-2-furaldehyde, 3,4-diacetoxy-1-butene, 4-acetoxybenezoic acid, vanillin acetate, propylene glycol methyl ether acetate, methyl lactate, ethyl lactate, methyl glycolate, ethyl glycolate, methyl methoxyacetate, ethyl methoxyacetate, methyl 3-hydroxybutyrate, ethyl 3-hydroxybutyrate, and triethyl 2-acetyl citrate.

In yet another implementation, the acyl donors are selected from monoacetin, diacetin, triacetin, monopropionin, dipropionin, tripropionin, monobutyrin, dibutyrin, tributyrin, glucose pentaacetate, xylose tetraacetate, acetylated xylan, acetylated xylan fragments, β-D-ribofuranose-1,2,3,5-tetraacetate, tri-O-acetyl-D-galactal, tri-O-acetyl-D-glucal, monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,5-pentanediol, 1,6-pentanediol, 1,2-hexanediol, 2,5-hexanediol, 1,6-hexanediol, and mixtures thereof. In a further implementation, the acyl donor is propylene glycol diacetate (PGDA), ethylene glycol diacetate (EGDA), or a mixture thereof. In yet another implementation, the acyl donors are selected from monoacetin, diacetin, triacetin, monopropionin, dipropionin, tripropionin, monobutyrin, dibutyrin, and tributyrin. In yet another aspect, the acyl donor is selected from diacetin and triacetin.

The amount or concentration of the acyl donor may vary widely. In at least one implementation, the amount of the acyl donor may be at least partially determined by a target or desired concentration of peroxyacid or peracetic acid to be generated via enzyme-catalyzed perhydrolysis. For example, the target or desired concentration of peroxyacid or peracetic acid to be generated via enzyme-catalyzed perhydrolysis may be less than or equal to about 2,000 ppm, and the amount of the acyl donor present in the oral care whitening composition may be greater than or equal to 0.05 wt % and less than or equal to 40 wt % based on a total weight of the oral care whitening composition. For example, the amount of the acyl donor present in the oral care whitening composition may be from about 0.05 wt %, about 5 wt %, about 10 wt %, about 15 wt %, about 20 wt %, or about 25 wt % to about 30 wt %, about 35 wt %, or about 40 wt %. In another implementation, the amount of the acyl donor present in the oral care whitening composition may be less than 2 wt %. For example, the amount of the acyl donor present in the oral care whitening composition may be less than 10 wt %, less than 9.5 wt %, less than 9.0 wt %, less than 8.5 wt %, less than 8.0 wt %, less than 7.5 wt %, less than 7.0 wt %, less than 6.5 wt %, less than 6.0 wt %, less than 5.5 wt %, less than 5.0 wt %, less than 4.5 wt %, less than 4.0 wt %, less than 3.5 wt %, less than 3.0 wt %, less than 2.5 wt %, less than 2.0 wt %, less than 1.5 wt %, less than 1.0 wt %, less than 0.9 wt %, less than 0.8 wt %, less than 0.7 wt %, less than 0.6 wt %, less than 0.5 wt %, less than 0.4 wt %, less than 0.3 wt %, less than 0.2 wt %, or less than 0.1 wt %. In a typical implementation, the amount of the acyl donor present in the oral care whitening composition may be greater than or equal to about 0.5 wt % and less than or equal to about 1.3 wt %.

Enzymes Having Perhydolytic Activity

The oral care composition of the present disclosure may include one or more enzymes having perhydolytic activity. The one or more enzymes having perhydolytic activity include any enzyme capable of catalyzing a reaction between the one or more sources of hydrogen peroxide or the hydrogen peroxide generated therefrom as described herein and a suitable substrate, i.e., an acyl donor of the present disclosure, to generate an oral care whitening enhancer. Typically, the enzyme is a perhydrolase. Perhydrolases are enzymes that generate peroxyacid via perhydrolysis. In enzyme-catalyzed perhydrolysis reactions, the acyl donor substrate (a peroxyacid precursor) is combined with a source of hydrogen peroxide and water. The perhydrolase catalyzes the formation of a peroxyacid, such as peracetic acid.

Enzymes having perhydrolytic activity include certain lipases, proteases, esterases, acyl transferases, aryl esterases, carbohydrate esterases, and combinations thereof. Examples include the perhydrolytic proteases disclosed in U.S. Pat. No. 7,510,859, which is herein incorporated by reference in its entirety, the perhydrolytic aryl esterases disclosed in U.S. Pat. No. 8,663,616, which is herein incorporated by reference in its entirety and the perhydrolytic aryl esterase/acyl transferase from *Mycobacterium smegmatis*, which is disclosed in U.S. Pat. No. 8,663,616. Typically, the perhydrolase is a perhydrolase carbohydrate esterase.

Even more typically, the perhydrolase carbohydrate esterase suitable for inclusion in the present oral care whitening compositions is a member of the carbohydrate esterase family 7 (CE-7). Enzymes from the CE-7 family are well known in the art (see Coutinho, P. M., Henrissat, B. "Carbohydrate-active enzymes: an integrated database approach" in Recent Advances in Carbohydrate Bioengineering, H. J. Gilbert, G. Davies, B. Henrissat and B. Svensson eds., (1999) The Royal Society of Chemistry, Cambridge, pp. 3-12, which is herein incorporated by reference in its entirety). The CE-7 family of enzymes has been demonstrated to be particularly effective for producing peroxyacids acids from a variety of acyl donor substrates when combined with a source of peroxygen, e.g., hydrogen peroxide (U.S. Pat. Nos. 7,794,378; 7,951,566; 7,723,083; and 7,964,378 and U.S. Patent Application Publication Nos. 2008-0176299, 2010-0087529, 2011-0081693, and 2011-0236335 to DiCosimo et al.; each incorporated herein by reference in its entirety).

Members of the CE-7 family, which include, e.g., cephalosporin C deacetylases (CAHs; E.C. 3.1.1.41) and acetyl xylan esterases (AXEs; E.C. 3.1.1.72), share a conserved signature motif (Vincent et al., *J. Mol. Biol.*, 330:593-606 (2003), which is herein incorporated by reference in its entirety). The signature motif for CE-7 family members comprises three conserved motifs as follows (residue position numbering relative to reference sequence SEQ ID NO: 2; the CE-7 perhydrolase from *B. subtilis* ATCC® 31954™). The relative numbering accounts for small insertions or deletions (for example, typically five amino acids of less) within the aligned sequence.

The CE-7 signature motif includes: a) arginine ("Arg" or "R") at position 118, glycine ("Gly" or "G") at position 119 and glutamine ("Gln" or "Q") at position 120 of SEQ ID NO: 2; b) G at position 179, any amino acid ("XAA" or "X") at position 180, serine ("Ser" or "S") at position 181, Q at position 182 and G at position 183 of SEQ ID NO: 2; and c) histidine ("His" or "H") at position 298 and glutamic acid ("Glu" or "E") at position 299 of SEQ ID NO: 2.

Typically, the X at amino acid residue position 180 is glycine, alanine ("Ala" or "A"), proline ("Pro" or "P"), tryptophan ("Trp" or "W") or threonine ("Thr" or "T"). In some implementations, the X at amino acid residue position 180 is selected from the group consisting of glycine, alanine, proline, tryptophan, and threonine.

Further analysis of the conserved motifs within the CE-7 family indicates the presence of an additional conserved motif (Leucine ("Leu" or "L"), X and aspartic acid ("Asp" or "D"), i.e., LXD at amino acid positions 267-269 of SEQ ID NO: 2, that may be used to further define a perhydrolase belonging to the CE-7 carbohydrate esterase family. The X at amino acid residue position 268 is typically isoleucine ("Ile" or "I"), valine "Val" or "V" or methionine ("Met" or "M").

A number of well-known global alignment algorithms (i.e., sequence analysis software) may be used to align two or more amino acid sequences representing enzymes having perhydrolase activity to determine if the enzyme is comprised of the present signature motif. The aligned sequence(s) are compared to the reference sequence (SEQ ID NO: 2) to determine the existence of the signature motif.

In some implementations, a CLUSTAL alignment (such as CLUSTALW, e.g., version 1.83) using a reference amino acid sequence (as used herein the perhydrolase sequence, SEQ ID NO: 2) from the *Bacillus subtilis* ATCC® 31954™) is used to identify perhydrolases belonging to the CE-7 family. CLUSTAL is a series of widely used computer programs in bioinformatics for multiple sequence alignment and is described, for example, in Larkin et al., *Bioinformatics*, 2007 23(21): 2947-2948. doi:10.1093/bioinformatics/btm404, see also Higgins and Sharp, CABIOS, 5:151-153 (1989); Higgins et al., Nucleic Acids Res. 22:4673-4680 (1994); and Chema et al., Nucleic Acids Res 31 (13):3497-500 (2003)), which are each incorporated herein by reference in its entirety.

CLUSTAL (such as CLUSTALW, e.g., version 1.83 or CLUSTAL OMEGA e.g., version 1.2.3), is available from the European Molecular Biology Laboratory via the European Bioinformatics Institute. Suitable parameters for CLUSTALW or CLUSTAL OMEGA protein alignments include default parameters. Other suitable parameters for CLUSTAL W include GAP Existence penalty=15, GAP extension=0.2, matrix=Gonnet (e.g., Gonnet250), protein ENDGAP=-1, protein GAPDIST=4, and KTUPLE=1. In some implementations, a fast or slow alignment is used with the default settings where a slow alignment is more desirable. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

Examples of other suitable algorithms that may be used to identify sequences comprising the present signature motif (when compared to the reference sequence) include, but are not limited to, Needleman and Wunsch (J. Mol. Biol. 48, 443-453 (1970); a global alignment tool) and Smith-Waterman (J. Mol. Biol. 147:195-197 (1981); a local alignment tool). In some implementations, a Smith-Waterman alignment is used with default parameters. An example of suitable default parameters include the use of a BLOSUM62 scoring matrix with GAP open penalty=10 and a GAP extension penalty=0.5.

Typically, the oral care compositions of the present disclosure include one or more enzymes that comprise a CE-7 signature motif that aligns with SEQ ID NO: 2 using, e.g., CLUSTALW, the CE-7 signature motif comprising a) an RGQ motif at positions corresponding to positions 118-120 of SEQ ID NO: 2; b) a GXSQG (SEQ ID NO: 3) motif at positions corresponding to positions 179-183 of SEQ ID NO: 2 and a HE motif at positions corresponding to positions 298-299 of SEQ ID NO:2.

In some implementations, the enzyme used in the present oral care compositions is a "CE-7 variant", i.e., a CE-7 perhydrolase having a genetic modification that results in at least one amino acid addition, deletion, and/or substitution when compared to the corresponding enzyme (typically a wild type CE enzyme) from which the variant was derived; so long as the CE-7 signature motif and the associated perhydrolytic activity are retained. Examples of CE-7 variants suitable for use in the present oral care compositions are provided in U.S. Pat. No. 8,663,616, which is herein incorporated by reference in its entirety. A typical variant for use in the present oral care compositions is SEQ ID NO: 1, wherein a serine is substituted for the cysteine present at position 277 in wild type *Thermotoga maritima* perhydrolase.

In some implementations, the perhydrolase of the present disclosure is a CE-7 variant comprising the CE-7 signature motif and having at least 33%, more typically at least 40%, more typically at least 42%, more typically at least 50%, more typically at least 60%, more typically at least 70%, more typically at least 80%, more typically at least 90%, and yet even more typically at least 90%, 91%, 92%, 93%, 94%, 95%, 96%, 97%, 98%, or 99% amino acid identity to SEQ ID NO: 1 (EZ-1) or SEQ ID NO: 2. In some implementations, the oral care compositions of the present disclosure include an enzyme comprising an amino acid sequence having at least 80% amino acid sequence identity to SEQ ID NO:1. In other implementations, the oral care composition of the present disclosure includes an enzyme comprising the amino acid sequence of SEQ ID NO: 1.

As used herein the term "percent identity" refers to a relationship between two or more amino acid sequences (or polypeptide sequences, which is used interchangeably herein with the term "amino acid sequence") or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in: Biocomputing: Informatics and Genome Projects (Smith, D. W., ed.) Academic Press, NY (1993). Methods to determine identity are codified in publicly available computer programs, such as CLUSTALW or CLUSTAL OMEGA as described herein and as well known in the art.

The skilled artisan recognizes that variants of SEQ ID NO: 1, other CE-7 variants or SEQ ID NO: 2 (retaining the signature motifs) may also be obtained by hybridization. For example, variants of, e.g., SEQ ID NO: 1 may be identified by their ability to hybridize, under highly stringent conditions with the nucleic acid molecules associated with the amino acid sequence of SEQ ID NO: 1.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms.

Post-hybridization washes generally determine stringency conditions. Typically, the washing conditions include a series of washes starting with 6×SSC, 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. A more typical set of conditions uses higher temperatures in which the washes are identical to those above except for the temperature of the final two 30 minute washes in 0.2×SSC, 0.5% SDS was increased to 60° C. Another typical set of highly stringent hybridization conditions includes 0.1×SSC, 0.1% SDS, 65° C. and washed with 2×SSC, 0.1% SDS followed by a final wash 10, of 0.1% SSC, 0.1% SDS, 65° C.

In some implementations, variants of, e.g., SEQ ID NO: 1 comprising the above-identified CE-7 signature motifs, may be produced by mutagenesis. Various methods are known for mutating a nucleic acid sequence to produce a nucleic acid product with altered or enhanced activity including, but not limited to 1) random mutagenesis, 2) domain swapping (using zinc finger domains or restriction enzymes, 3) error-prone PCR (Melnikov at al., Nucleic Acids Research 27(4):1056-1062 (1999)); 4) site directed mutagenesis (Coombs at al., Proteins (1998), pp 259-311); and 5) "gene shuffling" (U.S. Pat. Nos. 5,605,793; 5,811, 238; 5,830,721; and 5,837,458, incorporated herein by reference). Proposed modifications are well within the routine skill in the art, as is determination of retention of biological activity of the encoded products.

In some implementations, the variants of, e.g., SEQ ID NO: 1 may demonstrate improved perhydrolysis activity in comparison to wild type enzymes or in comparison to SEQ ID NO: 1. Preparation of such variants may include, e.g., construction of an expression vector comprising the nucleotide sequence encoding a polypeptide that is structurally classified as a CE-7 enzyme or SEQ ID NO: 1, mutagenesis of the enzyme coding sequence, and finally isolation of variants with increased peroxyacid, such as peracetic acid, generation activity. Subsequent rounds of mutagenesis, if desired, allow for evolution of the enzyme-coding sequence. If desired, the regions of an enzyme important for enzymatic activity can be determined through routine site-directed mutagenesis, expression of the resulting variant polypeptides, and determination of their activities. Mutants may include deletions, insertions and point mutations, or combinations thereof.

The enzyme powder may have a particle size median diameter (D50) from about 100 µm to about 300 µm. For example, the particle size median diameter (D50) of the enzyme may be from about 100 µm, about 110 µm, about 120 µm, about 130 µm, about 140 µm, about 150 µm, about 160 µm, about 170 µm, about 180 µm, about 190 µm, or about 200 µm to about 210 µm, about 220 µm, about 230 µm, about 240 µm, about 250 µm, about 260 µm, about 270 µm, about 280 µm, about 290 µm, or about 300 µm. In another example, the enzyme may have a particle size median diameter (D50) from about 100 µm to about 300 µm, about 110 µm to about 290 µm, about 120 µm to about 280 µm, about 130 µm to about 270 µm, about 140 µm to about 260 µm, about 150 µm to about 250 µm, about 160 µm to about 240 µm, about 170 µm to about 230 µm, about 180 µm to about 220 µm, about 190 µm to about 210 µm.

The enzyme may be provided in the form of a powder, an enzyme powder, or a stabilized enzyme powder. Methods for making and stabilizing the enzyme powder are described in U.S. Patent Application Publication Nos. 2010-0086534 and 2010-0086535, the disclosures of which are incorporated herein by reference. The enzyme may be present in the enzyme powder in an amount of about 0.5 wt % to about 75 wt %, based on a dry weight of the enzyme powder. In a typical implementation, the enzyme may be present in the enzyme powder in an amount of about 10 wt % to about 50 wt %, or more typically in an amount of about 20 wt % to about 33 wt %, based on a dry weight of the enzyme powder.

The enzyme powder may include an excipient. The excipient may be or provide the balance of the enzyme powder. Accordingly, in at least one example, the enzyme powder may include only the enzyme and the excipient. In another example, the enzyme powder may include the enzyme, the excipient, and at least one additional component. The excipient may be an oligosaccharide having a number average molecular weight of at least about 1,250 and a weight average molecular weight of at least about 9,000. The oligosaccharide excipient may have a number average molecular weight of at least about 1,700 and a weight average molecular weight of at least about 15,000. Illustrative oligosaccharides may be or include, but are not limited to, maltodextrin, xylan, mannan, fucoidan, galactomannan, chitosan, raffinose, stachyose, pectin, insulin, levan, graminan, amylopectin, sucrose, lactulose, lactose, maltose, trehalose, cellobiose, nigerotriose, maltotriose, melezitose, maltotriulose, raffinose, kestose, and the like, and cominations or mixtures thereof. The oligosaccharides may also include, but are not limited to, water-soluble non-ionic cellulose ethers, such as hydroxymethyl-cellulose and hydroxypropylmethylcellulose, and mixtures thereof. The one or more excipients may be or include, but are not limited to, trehalose, lactose, sucrose, mannitol, sorbitol, glucose, cellobiose, α-cyclodextrin, carboxymethylcellulose, and the like, and combinations thereof. In a typical implementation, the oligosaccharide excipient is maltodextrin.

Oral Care Whitening Enhancer

As discussed above, the one or more enzymes having perhydolytic activity may catalyze, be capable of catalyzing, or be configured to catalyze a reaction between the one or more sources of hydrogen peroxide and the one or more acyl donors to generate the oral care whitening enhancer. In at least one implementation, the oral care whitening enhancer is peroxyacid or peracetic acid. The amount or concentration of the peracetic acid generated by perhydrolysis may vary widely. In at least one implementation, the amount of the peracetic acid generated may be from about 0.1 ppm to about 10,000 ppm based on a total weight of the oral care product (e.g., dentifrice) or the oral care composition thereof. For example, the amount of the peracetic acid generated may be from about 0.1 ppm, about 0.5 ppm, about 1 ppm, about 5 ppm, about 10 ppm, about 15 ppm, about 20 ppm, about 50 ppm, about 100 ppm, about 150 ppm, about 200 ppm, about 300 ppm, about 500 ppm, about 600 ppm, about 700 ppm, about 800 ppm, or about 900 ppm to about 1,000 ppm, about 1,200 ppm, about 1,400 ppm, about 1,600 ppm, about 1,800 ppm, about 2,000 ppm, about 2,500 ppm, about 3,000 ppm, about 3,500 ppm, about 4,000 ppm, about 5,000 ppm, about 6,000 ppm, about 7,000 ppm, about 8,000 ppm, about 9,000 ppm, or about 10,000 ppm. In another example, the amount of the peracetic acid generated may be less than 0.1 ppm, less than 0.5 ppm, less than 1 ppm, less than 5 ppm, less than 10 ppm, less than 15 ppm, less than 20 ppm, less than 50 ppm, less than 100 ppm, less than 150 ppm, less than 200 ppm, less than 300 ppm, less than 500 ppm, less than 600 ppm, less than 700 ppm, less than 800 ppm, less than 900 ppm, less than 1,000 ppm, less than 1,200 ppm, less than 1,400 ppm, less than 1,600 ppm, less than 1,800 ppm, less than 2,000 ppm, less than 2,500 ppm, less than 3,000 ppm, less than 3,500 ppm, less than 4,000 ppm, less than 5,000 ppm, less than 6,000 ppm, less than 7,000 ppm, less than 8,000 ppm, less than 9,000 ppm, or less than 10,000 ppm. In a typical implementation, the amount of the peracetic acid generated is less than 2000 ppm based on a total weight of the oral care product or the oral care composition thereof.

The whitening enhancer of the oral care composition may be generated within at least 3 minutes (min) from contacting the one or more sources of hydrogen peroxide, the one or more acyl donors, and/or the one or more enzymes having perhydolytic activity with one another or initiation of the perhydrolysis reaction. For example, the whitening enhancer of the oral care composition may be generated in less than or equal to 3 min, less than or equal to 2.8 min, less than or equal to 2.6 min, less than or equal to 2.4 min, less than or equal to 2.2 min, less than or equal to 2.0 min, less than or equal to 1.8 min, less than or equal to 1.6 min, less than or equal to 1.4 min, less than or equal to 1.2 min, less than or equal to 1.0 min, less than or equal to 0.8 min, less than or equal to 0.6 min, or less than or equal to 0.4 min.

Thickening System

The oral care composition may include a thickening system having one or more thickeners. The one or more thickeners may be any orally acceptable thickener or thickening agent. Illustrative thickeners may be or include, but are not limited to, colloidal silica, fumed silica, cross-linked polyvinylpyrrolidone (PVP), and the like, and mixtures or combinations thereof. In a typical implementation, the thickening system includes fumed silica. In at least one implementation, the oral composition may include additional and/or optional thickeners. Illustrative additional or optional thickeners may be or include, but are not limited to, carbomers (e.g., carboxyvinyl polymers), carrageenans (e.g., Irish moss, carrageenan, iota-carrageenan, etc.), high molecular weight polyethylene glycols (e.g., CARBO-WAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, and the like, and mixtures or combinations thereof.

In at least one implementation, the thickening system may include a single thickener. In one example, the thickening system may typically include fumed silica. In another implementation, the thickening system may include a plurality of thickeners. For example, the thickening system including a plurality of thickeners may typically include a silica thickener and a cross-linked PVP thickener. In another example, the thickening system may include a plurality of silica thickeners.

The amount or concentration of the thickening system and/or the thickeners thereof present in the oral care composition may vary widely. In at least one implementation, the amount of the thickening system and/or the thickeners thereof present in the oral care system may from about 2.0 wt % to about 6.0 wt % based on the total weight of the oral care composition. For example, the amount of the thickening system and/or the thickeners thereof present in the oral care system may be from about 2.0 wt %, about 2.2 wt %, about 2.4 wt %, about 2.6 wt %, about 2.8 wt %, about 3.0 wt %, about 3.2 wt %, about 3.4 wt %, about 3.6 wt %, or about 3.8 wt % to about 4.0 wt %, about 4.2 wt %, about 4.4 wt %, about 4.6 wt %, about 4.8 wt %, about 5.0 wt %, about 5.2 wt %, about 5.4 wt %, about 5.6 wt %, about 5.8 wt %, or about 6.0 wt %. In another example, the amount of the thickening system and/or the thickeners thereof present in the oral care system may be about 2.0 wt % to about 6.0 wt %, about 2.2 wt % to about 5.8 wt %, about 2.4 wt % to about 5.6 wt %, about 2.6 wt % to about 5.4 wt %, about 2.8 wt % to about 5.2 wt %, about 3.0 wt % to about 5.0 wt %, about 3.2 wt % to about 4.8 wt %, about 3.4 wt % to about 4.6 wt %, about 3.6 wt % to about 4.4 wt %, or about 3.8 wt % to about 4.2 wt %. In another example, the amount of the thickening system and/or the thickeners thereof present in the oral care system may be greater than 2.0 wt % and less than 2.6 wt %, less than 2.8 wt %, less than 3.0 wt %, less than 3.2 wt %, less than 3.4 wt %, less than 3.6 wt %, less than 3.8 wt %, less than 4.0 wt %, less than 4.2 wt %, less than 4.4 wt %, less than 4.6 wt %, less than 4.8 wt %, less than 5.0 wt %, less than 5.2 wt %, less than 5.4 wt %, less than 5.6 wt %, less than 5.8 wt %, or less than 6.0 wt %. In a typical implementation, the amount of the thickening system and/or the thickeners thereof present in the oral care system may be greater than or equal to about 2.5 wt % and less than or equal to about 5.0 wt % based on the weight of the composition.

As discussed above, in at least one implementation, the thickening system may include a plurality of thickeners. In at least one implementation, a first thickener may be present in the oral care system in an amount from about 2.5 wt % to about 4.5 wt % based on a total weight of the oral care composition, and a second thickener may be present in an amount from about 1 wt % to about 3.5 wt % based on a total weight of the oral care composition. In another implementation, the first thickener may be present in the oral care system in an amount from about 2.5 wt % to about 4.5 wt % based on a total weight of the oral care composition, and a second thickener may be present in an amount from about 1.5 wt % to about 3.0 wt % based on a total weight of the oral care composition.

In at least one implementation, the amount or concentration of the additional and/or optional thickeners present in the oral care composition may be from about 0.1 wt % to about 50 wt %, based on a total weight of the oral care composition. For example, the amount of the additional and/or optional thickeners present in the oral care system may be from about 0.1 wt %, about 0.5 wt %, about 1.0 wt %, about 1.5 wt %, about 2.0 wt %, about 2.5 wt %, about 3.0 wt %, about 3.5 wt %, about 4.0 wt %, about 4.5 wt %, about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, about 10.0 wt %, about 15.0 wt %, about 20.0 wt %, about 25.0 wt %, about 30.0 wt %, about 35.0 wt %, or about 40.0 wt %. In an exemplary implementation, the amount of the additional and/or optional thickeners present in the oral care composition may be greater than or equal to about 0.1 wt % and less than or equal to about 35 wt %. In a typical implementation, the amount of the additional and/or optional thickeners present in the oral care composition may be greater than or equal to about 0.1 wt % and less than or equal to about 15 wt %.

Polymers

In at least one implementation, the oral care composition may include one or more polymers or polymer additives. For example, the oral care composition may include one or more polymer thickeners. Illustrative polymer thickeners may be or include, but are not limited to, block co-polymers or polyethylene glycol and polyethylene glycol (e.g., molecular weight of at least 5000 Da), and the like, and combinations thereof. In at least one implementation, the oral carewhitening composition includes a block co-polymer of ethylene oxide and propylene oxide represented by the formula (5),

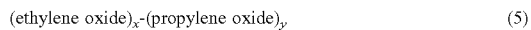

$$\text{(ethylene oxide)}_x\text{-(propylene oxide)}_y \qquad (5)$$

where x is an integer from about 80 to about 150 (e.g., x=100-130, or about 118), and y is an integer from about 30 to about 80 (e.g., y=60-70, or about 66). The block co-polymer of ethylene oxide and propylene oxide may have an average molecular weight greater than or equal to about 5,000 Da and less than or equal to about 20,000 Da. For example, the molecular weight of the block co-polymer of ethylene oxide and propylene oxide may be from about 8,000 Da to about 13,000 Da. In another example, the molecular weight of the block co-polymer of ethylene oxide and propylene oxide may be from about 9,800 Da or about 10,000 Da. In yet another example, the molecular weight of the block co-polymer of ethylene oxide and propylene oxide may be from about 8,000 Da to about 10,000 Da. In at least one implementation, the oral care composition does not include a block co-polymer of ethylene oxide and propylene oxide having a molecular weight less than 5,000 Da. For example, at least 99.5%, at least 99.0%, or at least 99.9% of the block co-polymer of ethylene oxide and propylene oxide present in the oral care composition has a molecular weight greater than or equal to 5,000 Da.

The amount or concentration of the polymers or polymer additives (e.g., block co-polymers) present in the oral care composition may vary widely. In at least one implementation, the amount of the polymers or polymer additives (e.g., block co-polymers) present in the oral care composition may be from about 5 wt % to about 10 wt %. For example, the amount of the polymers or polymer additives (e.g., block co-polymers) present in the oral care composition may be from about 5.0 wt %, about 5.5 wt %, about 6.0 wt %, about 6.5 wt %, about 7.0 wt %, or about 7.5 wt % to about 8.0 wt %, about 8.5 wt %, about 9.0 wt %, about 9.5 wt %, or about 10.0 wt %. In another example, the amount of the polymers or polymer additives present in the oral care composition may be from about 5.0 wt % to about 10.0 wt %, about 5.5 wt % to about 9.5 wt %, about 6.0 wt % to about 9.0 wt %, about 6.5 wt % to about 8.5 wt %, or about 7.0 wt % to about 8.0 wt %. In another implementation, the amount of the polymer or polymer additives present in the oral care composition may be from about 5 wt % to about 15 wt % based on a total weight of the composition. For example, the amount of the polymers or polymer additives (e.g., block co-polymers) present in the oral care composition may be from about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, or about 10.0 wt % to about 10.5 wt %, about 11.0 wt %, about 11.5 wt %, about 12.0 wt %, about 12.5 wt %, about 13.0 wt %, about 13.5 wt %, about 14.0 wt %, about 14.5 wt %, or about 15.0 wt %.

In at least one implementation, the polymers or polymer additives may be or include PLURACARE® L1220, which is commercially available from BASF of Wyandotte, Mich. In another implementation, the polymer or polymer additive may be or include polyethylene glycol (e.g., about 400-800 Da, or about 600 Da). In yet another implementation, the polymer or polymer additive may be or include a low or medium molecular weight polyethylene glycol having a molecular weight greater than or equal to about 400 Da and less than or equal to about 1000 Da. For example, the polymer or polymer additive may be or include PEG 400, PEG 600, PEG 800, PEG 100, and the like, and mixtures or combinations thereof. In at least one implementation, the oral care composition may include a stabilizing amount of an additional linear PVP.

Abrasives

In at least one implementation, the oral care composition may include an abrasive. Illustrative abrasives may be or include, but are not limited to, calcium abrasives, such as a calcium phosphate salt, pyrophosphate, dicalcium orthophosphate dihydrate, tricalcium phosphate, calcium polymetaphosphate, and the like, and combinations and mixtures thereof. In a typical implementation, the oral care composition includes a calcium abrasive, such as calcium pyrophosphate or calcium carbonate. In at least one implementation, the abrasive may be maintained in the dentifrice of the oral care composition.

In at least one implementation, the amount or concentration of the abrasives may be from about 5 wt % to about 20 wt %, based on a total weight of the oral care composition. For example, the amount of the abrasives present in the oral care composition may be from about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, about 10.0 wt %, about 10.5 wt %, about 11.0 wt %, about 11.5 wt %, or about 12.0 wt % to about 12.5 wt %, about 13.0 wt %, about 13.5 wt %, about 14.0 wt %, about 14.5 wt %, about 15.0 wt %, about 15.5 wt %, about 16.0 wt %, about 16.5 wt %, about 17.0 wt %, about 17.5 wt %, about 18.0 wt %, about 18.5 wt %, about 19.0 wt %, about 19.5 wt %, or about 20.0 wt %.

Vehicle

The oral care composition may form at least a portion of or be used in one or more oral care products. Illustrative oral care products may include, but are not limited to, a toothpaste (dentifrice), a prophylactic paste, a tooth powder, a tooth polish, a tooth gel (e.g., a whitening gel), a chewing gum, a lozenge, a mouthwash, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In a typical implementation, the oral care composition may form at least a portion of or be used with a toothpaste. For example, the oral care composition may typically be a gel of the toothpaste, or an gel to be combined with the toothpaste. The oral care composition may include or be combined with an orally acceptable vehicle to form the oral care product (e.g., the toothpaste). In an exemplary implementation, the orally acceptable vehicle may include glycerin.

In at least one implementation, the orally acceptable vehicle may include humectants, surface active agents, gelling agents, and the like, and combinations thereof. Illustrative humectants may be or include, but are not limited to, glycerin, propylene glycol, and combinations thereof. In at least one implementation, the humectant is present in an amount of from about 20 wt % to about 60 wt % based on a total weight of the oral care product. In at least one implementation, the oral care product and/or the oral care composition thereof is free or substantially free of polyol humectants. For example, the oral care product and/or the oral care composition thereof does not contain any polyols as a humetant. In another implementation, the propylene glycol is present in an amount of from about 10 wt % to about 20 wt % based on a total weight of the oral care product. In another implementation, the glycerin is present in an amount of from about 25 wt % to about 40 wt % based on a total weight of the oral care product.

In at least one implementation, the components of the oral care product may be combined with one another to provide the oral care product (e.g., toothpaste/dentifrice) with a target viscosity. As used herein, the term "viscosity" may refer to the internal resistance to flow exhibited by a fluid (e.g., water) or the ratio of shearing stress to rate of shear, and may be measured in poise or centipoise (cP). The viscosity of the various compositions discussed and described herein may be determined using a Viscometer at a temperature of about 25° C. In at least one implementation, the viscosity or target viscosity of the oral care product may be greater than or equal to about 10,000 cP and less than or equal to about 700,000 cP. For example, the viscosity or target viscosity of the oral care product may be about 10,000 cP, about 15,000 cP, about 20,000 cP, about 25,000 cP, or about 30,000 cP to about 35,000 cP, about 40,000 cP, about 50,000 cP, about 75,000 cP, about 100,000 cP, about 120,000 cP, about 150,000 cP, about 175,000 cP, about 200,000 cP, about 300,000 cP, about 400,000 cP, about 500,000 cP, about 600,000 cP, or about 700,000 cP. In a typical implementation, the viscosity of the oral care product is from about 30,000 cP to about 300,000 cP.

Fluoride Ion Source

The oral care products and/or the oral care composition thereof may further include one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In a typical implementation, the fluoride ion source includes sodium fluoride. The amount of the fluoride ion source in the oral care composition may be less than 0.08 wt %, less than 0.07 wt %, less than 0.06 wt %, less than 0.05 wt %, or less than 0.04 wt %. For example, the amount of the fluoride ion source may be about 0.05 wt %. In another implementation, the fluoride ion source is present in an amount to provide a total of about 100 to about 20,000 ppm, about 200 to about 5,000 ppm, or about 500 to about 2,500 ppm, fluoride ions.

Additional Ingredients

It should be appreciated to one having ordinary skill in the art, that the oral care products and/or the oral care composition thereof may include other orally acceptable additional ingredients/components. For example, the oral care products may include anti-caries agents, desensitizing agents, viscosity modifiers, diluents, surface active agents (e.g., surfactants, emulsifiers, foam modulators, etc.), pH modifying agents, humectants, mouth feel agents, sweetening agents, flavor agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials. Illustrative surface active agents or surfactants thereof may include, but are not limited to, water-soluble salts of $C_{8\text{-}20}$ alkyl sulfates, sulfonated monoglycerides of $C_{8\text{-}20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, cocoamidopropyl betaine, sodium lauryl sulfate (SLS), and the like, and combinations and mixtures thereof.

In at least one implementation, the additional ingredients/components may include one or more active materials configured to prevent and/or treat one or more conditions and/or disorders of the oral cavity. For example, the one or more active materials may be configured to prevent and/or treat one or more conditions and/or disorders of hard and/or soft tissue of the oral cavity. The active materials may also be configured to prevent and/or treat one or more physiological disorders and/or conditions, and/or provide a cosmetic benefit to the oral cavity.

In at least one implementation, the oral care products and/or the oral care composition thereof may include an anticalculus agent. Generally, anticalculus agents may not be compatible with some oral care compositions; however, implementations of the present disclosure may incorporate anticalculus agents and the oral care composition into a single phase oral care product. Illustrative anticalculus agents may include, but are not limited to, phosphates and polyphosphates (e.g., pyrophosphates), polyaminopropane-sulfonic acid (AMPS), hexametaphosphate salts, zinc citrate trihydrate, polypeptides, polyolefin sulfonates, polyolefin phosphates, diphosphonates. In a typical implementation, the anticalculus agents includes tetrasodium pyrophosphate (TSPP), sodium tripolyphosphate (STPP), or a combination thereof.

The oral care products and/or the oral care composition thereof may optionally include one or more further ingredients. For example, the oral care composition may include one or more antimicrobial agents and/or one or more preservatives such as, methylisothiazolinone (MIT), sodium benzoate, potassium sorbate, benzyl alcohol, and combinations thereof. In another example, the oral care composition may include one or more antibacterial agents selected from halogenated diphenyl ether (e.g. triclosan), herbal extracts and essential oils (e.g., rosemary extract, tea extract, *Magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, other metal ions (e.g., stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol, and other piperidino derivatives, nicin preparations, chlorite salts; and mixtures of any of the foregoing. In a typical implementation, the antibacterial agent includes cetylpyridinium chloride (CPC). For example, all of the dual-phase mouthwash compositions disclosed herein may include CPC as an antibacterial agent.

The oral care products and/or the oral care composition thereof may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and the like, and combinations and mixtures thereof.

Method

The present disclosure may provide methods for whitening the surfaces of teeth in a human or animal subject with an oral care product and/or the oral care whitening composition thereof. As used herein "animal subject" may include higher order non-human mammals such as canines, felines, and horses.

The method may include storing the oral care composition in a stable form until the time of use. The method may also include contacting the enzyme, the source of hydrogen peroxide, and/or the acyl donor of the oral care composition with one another to initiate the generation of peracetic acid. In at least one implementation, contacting the enzyme, the source of hydrogen peroxide, and/or the acyl donor of the oral care composition with one another to initiate the generation of peracetic acid may include admixing, stirring, or otherwise contacting a first phase (e.g., hydrophilic phase) containing any one or more of the sources of hydrogen peroxide, the acyl donors, and/or the enzymes having perhydolytic activity with a second phase (e.g., hydrophobic phase) containing the remaining one or more of the sources of hydrogen peroxide, the acyl donors, and/or the enzymes having perhydolytic activity. In another implementation, the source of hydrogen peroxide, and the acyl donor of the oral care composition may be contained in a single phase or a single oral care product, and initiating the generation of peracetic acid may include admixing, stirring, or otherwise contacting the enzyme, the source of hydrogen peroxide, and the acyl donor of the oral care composition with water (e.g., added water and/or water of the oral cavity). In at least one implementation, the method may include contacting the source of hydrogen peroxide with water to initiate the formation of hydrogen peroxide. The oral care composition may generate the peracetic acid within less than 2 min, less than 1.5 min, or less than 1 min. The method may also include contacting the surface of the teeth with the peracetic acid generated from the enzyme-catalyzed perhydrolysis of the source of hydrogen peroxide and the acyl donor.

In at least one implementation, the method for the oral care product including a single phase may include using the oral care product in a manner similar to the conventional oral care product. For example, the method for the oral care product including the single phase may include swishing the oral care product, brushing the teeth with the oral care product, disposing the dental tray in the oral cavity such that the contents thereof contact the surfaces of the teeth, and the like. The method for the oral care product including at least two phases may include contacting and/or combining a dentifrice (e.g., toothpaste) containing the source of hydrogen peroxide with an oral care booster containing the acyl donors and/or the enzymes having perhydolytic activity to form the oral care composition, and contacting the oral care composition with the surfaces of the teeth.

The oral care product and/or the oral care composition thereof may be applied and/or contacted with the surfaces of the teeth at predetermined intervals. For example, the oral care product and/or the oral care composition thereof may be applied and/or contacted with the surfaces of the teeth on a daily basis, at least one time a day for multiple days, or alternatively every other day. The oral care product and/or the oral care composition thereof may be utilized for up to 2 weeks, up to 3 weeks, up to 4 weeks, up to 6 weeks, up to 8 weeks, or greater.

All ingredients for use in the compositions described herein should be orally acceptable. By "orally acceptable" as the term is used herein is meant an ingredient that is present in a composition as described in an amount and form that does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The whitening efficacy of four oral care whitening compositions (1)-(4) is evaluated. To test the whitening efficacy of the four oral care whitening compositions (1)-(4), hydroxyapatite (HA) discs were exposed to a staining broth to stain the HA discs, and the stained HA discs were treated with each of the oral care whitening compositions (1)-(4).

The staining broth was prepared by combining equal parts by volume of a coffee stain solution, a tea stain solution, and a wine stain solution. To prepare the coffee stain solution, 1 g of instant coffee crystals was mixed with 100 g of heated deionized water for at least 15 min to completely dissolve the coffee crystals, and subsequently cooled to room temperature (RT). To prepare the tea stain solution, 1 tea bag (Lipton® Black Tea) was steeped in 100 g of heated deionized water for at least 15 min, and then cooled to RT. To prepare the wine stain solution, red wine was filtered through a fine mesh stainless steel filter to remove particulates.

To stain the HA discs, each HA disc was soaked in 1 mL of clarified, pooled, human saliva for three hours at about 37° C., and then transferred from the saliva to an individual centrifuge tube containing 5 mL of the staining broth. The HA discs were then soaked in the staining broth for three hours at about 37° C. The HA discs were then rinsed with 5 mL of deionized water twice to remove any of the staining broth that was not bound to the HA discs. After rinsing, the HA discs were air dried overnight in the dark, and the CIELAB values were then measured with a spectrophotometer (MINOLTA® CR300). Particularly, each side of each HA disc was measured and averaged to provide a baseline or reference color for each HA disc.

It should be appreciated that "CIELAB" is a color measurement system or standard adopted by the Commission Internationale de l'Eclairage (CIE) in 1976. It is based on a three-dimensional CIELAB color space. The system was developed to represent color in a manner that is consistent with human vision and proportional to perceived color differences. CIELAB values describe coordinates of a specific color in the three dimensional CIELAB color space. There are three axes: L* (defining light to dark); b* (defining blue to yellow); and a* (defining red to green). Any point in the three dimensional CIELAB color space may be defined by its L*, a*, and b* coordinates. The same point may also be defined by L*, hue angle, and chroma, which uses cylindrical coordinates. The hue angle is defined by the formula: $H_{ab} = \tan^{-1}(b^*/a^*)$, where a* and b* are coordinates in the L*a*b* three dimensional CIELAB color space. A detailed description of hue angle may be found in M. L. Gulrajani (Ed.), (2010). *Colour Measurement: Principles, Advances and Industrial Applications*. Cambridge, United Kingdom: Woodhouse Publishing, which is herein incorporated by reference in its entirety.

The four oral care whitening compositions (1)-(4) were prepared by combining the ingredients/components according to Table 1. To prepare each of the oral care whitening compositions a hydrogen peroxide (HP) toothpaste (e.g., dentifrice), having the composition indicated in Table 2, was combined with a 100 mM phosphate buffer (pH=7.4) at a ratio of about 1:2 to form a slurry or dentifrice. The slurry was prepared immediately before the HA discs were treated with the oral care whitening compositions (1)-(4).

TABLE 1

Oral care whitening Compositions

| Ingredient | (1) | (2) | (3) | (4) |
|---|---|---|---|---|
| Slurry | 1.0 wt % | 1.0 wt % | 1.0 wt % | 1.0 wt % |
| Triacetin | — | 1.29 wt % | 0.516 wt % | — |
| EZ-7 Enzyme | — | — | 0.004 wt % | — |
| Peracetic Acid (PAA) | — | — | — | 0.18 wt % |

TABLE 2

Composition of Hydrogen Peroxide (HP) Toothpaste

| Ingredient | Amount (wt %) |
|---|---|
| $PEG_{118}/PPG_{66}$ co-polymer (PLURACARE ® L1220F) | 7.5 |
| Glycerin | 28.36 |
| Humectants | 21.0 |
| PEG 600 | 10 |
| PVP | 2.5 |
| Thickener | 2.5 |
| Source of $H_2O_2$ | 5.5 |
| Abrasives | 15 |
| Anticalculus Agent | 2 |
| Sweetener | 0.65 |
| Fluoride Ion Source | 0.76 |
| Surfactants and/or Surface Active Agents | 2 |
| Antioxidant | 0.03 |
| 85 wt % syrupy phosphoric acid | 0.2 |
| Flavor | 2 |
| Total | 100 |

As indicated in Table 1, a negative control whitening composition (1) included only the slurry, and a positive control whitening composition (4) included the slurry and 0.18 wt % peracetic acid (PAA). As further indicated in Table 1, each of the test oral care whitening compositions (2) and (3) included the slurry and a respective oral care whitening booster. The whitening boosters tested in oral care whitening composition (2) included triacetin, and the whitening booster tested in oral care whitening composition (3) included triacetin and EZ-7 Enzyme.

To treat each of the HA discs, 2 mL of the slurry was combined with the respective oral care whitening booster and mixed or vortexed for 10 sec in a centrifuge tube. After combining the slurry with the whitening booster, each of the HA discs was added to the centrifuge tube and the HA disc was gently mixed or vortexed for 2 min to simulate brushing. After the HA disc was treated, the slurry was separated from the HA disc via an aspirator. The HA disc was then rinsed twice with deionized water and dried overnight in the dark. After drying, post-treatment CIELAB values were measured. Each of the HA discs were treated in triplicate.

The whitening efficacy (ΔWIO) of each of the oral care whitening compositions (1), (2), (3), and (4) are summarized below in Table 3.

TABLE 3

ΔWIO of Oral care whitening Compositions (1)-(4)

| (1) (ΔWIO) | (2) (ΔWIO) | (3) (ΔWIO) | (4) (ΔWIO) |
|---|---|---|---|
| −17.91 ± 3.69 | −20.15 ± 1.64 | −27.32 ± 1.33 | −26.30 ± 1.68 |

As is evident from Table 3, the oral care whitening compositions (3) and (4) exhibited relatively greater whitening efficacies (ΔWIO) than the control (1), which included only the slurry. The oral care whitening compositions (3) and (4) also exhibited relatively greater whitening efficacies (ΔWIO) than the oral care whitening composition (2). As is also evident from Table 3, the oral care whitening composition (3), which had a theoretical maximum production of peracetic acid of about 0.18 wt %, exhibited a whitening efficacy (ΔWIO) that was at parity to the oral care whitening composition (4) containing the slurry and peracetic acid. The results indicate that the in situ generation of peracetic acid is capable of providing comparable whitening efficacy (ΔWIO) as compared to the direct delivery of peracetic acid. The results also indicate that the in situ generation of peracetic acid is an effective method for delivering peracetic acid. The results further indicated that the addition of a perhydrolytic enzyme (e.g., the EZ-7 enzyme) catalyzes the production of peracetic acid in the presence of dentifrice ingredients.

Example 2

The stability of triacetin in an oral care whitening booster was evaluated. A whitening booster gel composition (5) was prepared by combining the ingredients/components according to Table 4. To test the stability of the triacetin in the whitening booster gel composition (5), the amount of unreacted triacetin in the whitening booster gel composition (5) was measured over a period of 91 days at room temperature (RT) and at 40° C. via HPLC.

TABLE 4

Booster Gel Composition

| Ingredients/Components | Weight Percent (wt %) |
|---|---|
| Glyceryl Triacetate | 70.875 |
| Tetrasodium Pyrophosphate | 2.500 |
| Sodium Acid Pyrophosphate | 0.500 |
| Pluronic L1220 | 10.000 |
| Fumed Silica | 5.000 |
| Pyolyvinyl Pyrrolidone | 8.000 |
| Spray-Dried EZ1 in Triacetin | 3.125 |

TABLE 5

Stability of Triacetin in Booster Gel Formula

| Temp | Days | | | | | | | | | | | |
|---|---|---|---|---|---|---|---|---|---|---|---|---|
| | 0 | 5 | 14 | 28 | 36 | 42 | 56 | 63 | 70 | 76 | 83 | 91 |
| RT | 100.0 | 100.9 | 96.9 | 99.0 | 101.8 | 98.5 | 99.9 | — | 94.7 | 96.4 | 95.9 | 95.4 |
| 40° C. | 100.0 | 100.7 | 99.0 | 97.2 | 103.3 | 96.6 | 97.5 | 95.1 | 97.9 | 95.3 | 96.0 | 95.9 |

As illustrated in Table 5, the amount of triacetin measured at room temperature and 40° C. was stable over the 91 days, thereby indicating that the triacetin was stable in the oral care whitening booster gel composition (5) at accelerated conditions.

The amount of PAA generated in the booster gel composition (5) was evaluated via HPLC and UV/Vis. Since PAA is not visible via UV-Vis, secondary compounds that are visible or absorb in the UV-Vis spectrum were derived from the generated PAA via successive oxidation reactions. To derive the secondary compounds, about 0.5 g of the booster gel composition (5) was mixed with 0.5 g of a phosphate buffer solution (pH=7.0) for two minutes. 360 µl of the resulting solution/mixture were then transferred to a microfuge tube containing 40 µl of 1.3 M phosphoric acid and mixed or agitated to reach a final pH of less than 3, thereby terminating the enzymatic reaction. 100 µl of clarified supernatant was then transferred to an HPLC container/vial containing 300 µl of water and 100 µl of a methyl tolyl sulfide (MTS) reagent, and mixed or agitated in the dark for at least 10 min, thereby reacting the PAA with the MTS reagent to produce methyl tolyl sulfoxide (MTSO) and acetic acid (AcOH). Then 400 µl of acetonitrile and 100 µl of a triphenyl phosphine (TPP) reagent was added to the solution and allowed to react in the dark for 30 min. After 30 min, 100 µl of acetonitrile was added and mixed thoroughly, and the resulting solution was analyzed via HPLC. The calculated concentration of MTSO was then corrected for dilution (i.e., during the acid quench step), concentration (i.e., during the centrifugation step), and total reaction volume. It should be appreciated that the concentration of PAA is equivalent to the calculated concentration of MTSO including the aforementioned corrections. The amount of PAA generated from the oral care whitening booster gel composition (5) is summarized in Table 6, and further demonstrates the stability of the enzyme system.

TABLE 6

Amount of Peracetic Acid (PAA) in the Booster Gel Composition (5)

| | Days at RT | | |
|---|---|---|---|
| | 57 | 70 | 91 |
| PPA (ppm) | 335 | 395 | 451 |

Example 3

The stability (e.g., thermal stability) of the booster gel composition (5) of Example 2 was evaluated in the presence and absence of propylene glycol via microcalorimetry. The compositions of the booster gel composition with propylene glycol (6) and without propylene glycol (7) are summarized in Table 7. The results of the microcalorimetry study of the booster gel compositions (6) and (7) are summarized in Table 8.

TABLE 7

Composition of Booster Gels (6) and (7)

| Ingredients/Components | (6) Booster Gel w/Propylene Glycol | (7) Booster Gel w/out Propylene Glycol |
|---|---|---|
| EZ1 | 0.2 wt % | 0.2 wt % |
| Triacetin | 57.3 wt % | 71 wt % |
| Propylene Glycol | 14% | — |

TABLE 8

Thermal Activity Monitor (TAM) Microcalorimetry Data

| Sample | Heat Flow (µW/g) | Triacetin Stability |
|---|---|---|
| (6) | 10.7 | Unstable |
| (7) | 0.10 | Stable |

As indicated in Table 8, it was surprisingly and unexpectedly discovered that the presence of propylene glycol reduced the thermal stability of triacetin in the booster gel composition (6). Particularly, it was surprisingly and unexpectedly discovered that replacing the propylene glycol with triacetin, as indicated in booster gel composition (7), increased the stability thereof.

Example 4

An in vitro brushing study of the oral care whitening booster composition (5) of Example 2 was conducted. Particularly, artificially stained bovine incisors individually mounted to resin blocks were obtained from Therametric Technologies, Inc. The artificially stained bovine teeth were prophied with a silica abrasive dentifrice until the L*, a*, b* values were comparable to naturally stained human teeth. All measurements were taken using a hand-held spectrophotometer. Trays of the teeth were prepared. Each tray contained four teeth mounted using an impression compound. Heads of manual toothbrushes were removed from their handles and mounted on a brushing assembly/machine. 1:1 slurries of dentifrice to artificial saliva were prepared. Toothpaste slurries were freshly prepared for each individual treatment. 25 grams of the slurry was added to each tray and brushing was initiated immediately. The teeth were brushed for a total of 2 minutes with 250 grams of pressure at a rate of 120 strokes per minute. After brushing was terminated, the slurry was removed, and residual toothpaste was rinsed away with 100 grams of deionized water. The teeth were then gently blotted with a paper towel to remove any excess liquids and measurements were taken with the hand-held spectrophotometer. The brushing treatment and measurement cycle was repeated for a total of 14 times to mimic twice daily use of each product for 7 days. Eight of the teeth were tested with each product.

The L*, a*, b* values after treatment were compared to the baseline values to calculate the change in the whiteness of each of the teeth. The change in whiteness index ($\Delta W^*$) is summarized in Table 9. It should be appreciated that the whiteness index ($W^*$) is a measure of overall color change relative to pure white, and is given by formula (7), and the change in whiteness index ($\Delta W^*$) is measured by formula (8). It should further be appreciated that the more negative the value of $\Delta W^*$, the closer the tooth color is to white.

$$W^* = ((L^* - 100)^2 + (a^*)^2 + (b^*)^2)^{1/2} \tag{7}$$

$$\Delta W^* = W^*\text{treated} - W^*\text{baseline} \tag{8}$$

TABLE 9

Oral care whitening Efficacy (ΔW*) for In Vitro Brushing Treatments

| | | Number of Brushing Treatments | | | | | | | |
|---|---|---|---|---|---|---|---|---|---|
| | | 0 | 2 | 4 | 6 | 8 | 10 | 12 | 14 |
| 0.1% HP Toothpaste with Booster Gel | ΔW* | 0 | −2.50 | −3.90 | −5.00 | −5.59 | −6.36 | −6.93 | −7.43 |
| | Std. Dev | 0 | 1.09 | 1.57 | 1.86 | 2.08 | 2.09 | 2.24 | 2.13 |
| 1.0% HP Toothpaste | ΔW* | 0 | −2.49 | −3.53 | −4.16 | −4.65 | −5.81 | −6.19 | −6.71 |
| | Std. Dev | 0 | 0.35 | 0.46 | 0.45 | 0.51 | 0.36 | 0.37 | 0.43 |
| 0.1% HP Toothpaste | ΔW* | 0 | −1.51 | −2.34 | −3.06 | −3.77 | −4.03 | −4.31 | −4.60 |
| | Std. Dev | 0 | 0.59 | 1.06 | 0.95 | 1.26 | 1.22 | 1.35 | 1.34 |

As illustrated in Table 9, the 0.1% HP toothpaste including the booster gel composition (5) whitened teeth faster and/or more efficiently, and also provided teeth that were closer to white.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An oral care product, comprising:
   a glycol-free gel, comprising:
   an acyl donor; and
   a perhydrolase enzyme that catalyzes the generation of peracetic acid between a source of hydrogen peroxide and an acyl donor; and
   a paste comprising a source of hydrogen peroxide.

2. The oral care product according to claim 1, wherein the source of hydrogen peroxide comprises a cross-linked polyvinylpyrrolidone (PVP) hydrogen peroxide complex.

3. The oral care composition according to claim 2, wherein the cross-linked polyvinylpyrrolidone (PVP) hydrogen peroxide complex is present in an amount of from about 0.1 wt. % to about 10 wt. %, of the oral care composition.

4. The oral care composition according to claim 1, wherein the source of hydrogen peroxide is present in an amount necessary to provide from about 0.05 wt. % to about 2 wt. %, of hydrogen peroxide.

5. The oral care product according to claim 1, wherein the paste is substantially anhydrous.

6. The oral care product according to claim 1, wherein the paste contains no added water.

7. The oral care product according to claim 1, wherein the glycol-free gel is substantially anhydrous.

8. The oral care product according to claim 1, wherein the perhydrolase enzyme is provided as a powder.

9. The oral care product according to claim 1, wherein the paste further comprises a thickening system.

10. The oral care product according to claim 9, wherein the thickening system comprises a thickener selected from: a cross-linked polyvinylpyrrolidone; silica; a carbomer; a cellulosic polymer; a natural gum; colloidal magnesium aluminum silicate; and a combination of two or more thereof.

11. The oral care product according to claim 1, further comprising a colorant.

12. The oral care product according to claim 11, wherein the colorant is selected from a blue dye; a blue pigment; and a combination thereof.

13. The oral care product according to claim 1, wherein the product provides greater than 500 ppm of peracetic acid during brushing.

14. The oral care product according to claim 1, wherein the composition provides greater than 500 ppm of peracetic acid within 2 minutes of contacting the oral cavity.

15. The oral care product according to claim 1, wherein the acyl donor remains stable for at least about 90 days at 40° C.

16. The oral care product according to claim 15, wherein the acyl donor comprises triacetin.

17. The oral care product according to claim 1, wherein the paste further comprises a calcium abrasive.

18. The oral care product according to claim 17, wherein the calcium abrasive comprises a calcium phosphate salt, calcium pyrophosphate, dicalcium orthophosphate dihydrate, tricalcium phosphate, calcium polymetaphosphate, or combinations thereof.

19. The oral care product according to claim 1, wherein the glycol-free gel further comprises an anti-calculus agent.

20. The oral care product according to claim 19, wherein the anti-calculus agent comprises a phosphate selected from: tetrasodium pyrophosphate; sodium tripolyphosphate; a hexametaphosphate salt; polyaminopropanesulfonic acid (AMPS); polyolefin phosphates; diphosphonates; and a combination of two or more thereof.

* * * * *